(12) United States Patent
Amanullah et al.

(10) Patent No.: US 9,164,018 B2
(45) Date of Patent: Oct. 20, 2015

(54) METHOD FOR PREDICTION OF INHIBITION DURABILITY INDEX OF SHALE INHIBITORS AND INHIBITIVE DRILLING MUD SYSTEMS

(71) Applicant: Saudi Arabian Oil Company, Dhahran (SA)

(72) Inventors: Md Amanullah, Dhahran (SA);
Mohammed Al-Arfaj, Dammam (SA);
Adel Al-Ansari, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 195 days.

(21) Appl. No.: 13/854,638

(22) Filed: Apr. 1, 2013

(65) Prior Publication Data

US 2014/0295559 A1    Oct. 2, 2014

(51) Int. Cl.
*G01N 33/22* (2006.01)
*G01N 3/56* (2006.01)
*G01N 33/24* (2006.01)

(52) U.S. Cl.
CPC ............... *G01N 3/567* (2013.01); *G01N 33/24* (2013.01)

(58) Field of Classification Search
CPC .............................. G01N 3/567; G01N 33/24
USPC ........................................ 436/2, 25; 175/72
See application file for complete search history.

(56) References Cited

U.S. PATENT DOCUMENTS

| | | | |
|---|---|---|---|
| 3,953,336 A * | 4/1976 | Daigle | 507/114 |
| 4,142,595 A * | 3/1979 | Anderson et al. | 175/72 |
| 4,281,712 A * | 8/1981 | Murphy et al. | 166/254.2 |
| 4,507,210 A | 3/1985 | Lauzon | |
| 4,536,297 A * | 8/1985 | Loftin et al. | 507/121 |
| 4,757,862 A | 7/1988 | Naiman | |
| 5,635,458 A * | 6/1997 | Lee et al. | 507/240 |
| 6,020,282 A * | 2/2000 | Taylor et al. | 502/84 |
| 6,247,358 B1 | 6/2001 | Dos Santos | |
| 6,586,587 B1 | 7/2003 | Maas et al. | |
| 6,857,485 B2 | 2/2005 | Patel et al. | |
| 7,268,100 B2 | 9/2007 | Kippie et al. | |
| 7,312,183 B2 | 12/2007 | Patel et al. | |
| 7,605,112 B2 | 10/2009 | Orton et al. | |
| 7,786,049 B2 | 8/2010 | Temple et al. | |
| 7,825,072 B2 | 11/2010 | Carbajal et al. | |
| 7,829,506 B1 | 11/2010 | Tehranchi | |
| 2009/0131280 A1 | 5/2009 | Federici et al. | |

OTHER PUBLICATIONS

Nesbitt, L. E. et al, SPE paper 14248, 1985, 9 pages.*

(Continued)

*Primary Examiner* — Arlen Soderquist
(74) *Attorney, Agent, or Firm* — Bracewell & Guiliani LLP; Constance Gall Rhebergen; Brad Y. Chin (57) ABSTRACT

Embodiments of a method used for determination of inhibition durability index (IDI) of an inhibitive mud system can include multiple stages, with each stage including specific steps. The first stage can include a dispersion test that evaluates the inhibition effects of a stability inhibitor after exposing the test material to the inhibitor. The second stage can include a durability inhibition assessment, which includes assessing the longevity of the effect of the inhibitor. A third stage can be used to graph or otherwise evaluate the results of the second stage or the first and second stages.

14 Claims, 3 Drawing Sheets

(56) References Cited

OTHER PUBLICATIONS

PCT International Search Report and the Written Opinion of the International Searching Authority dated Jul. 3, 2014; International Application No. PCT/US2014/032462; International File Date: Apr. 1, 2014.

Anderson, D. B., Fluid Development for Drilling Sloughing and Heaving Shales; Engineering Profits Into Energy Operations; Sep. 1, 1977; pp. 105-106; vol. 49, No. 10; Petroleum Engineer Int.

Burba, III, J. L., et al., Laboratory and Field Evaluations of Novel Inorganic Drilling Fluid Additive; IADC/SPE 1988 Drilling Conference—Dallas, Texas; Feb. 28-Mar. 2, 1988; pp. 179-186; IADC/SPE Drilling Conference.

Tas, B. T., An Experimental Investigation of the Shale Inhibition Properties of a Quaternary Amine Compound; Feb. 1, 2013; pp. 21-24; A Thesis Submitted to the Graduate School of Natural and Applied Sciences of Middle East Technical University.

* cited by examiner

METHOD FOR PREDICTION OF INHIBITION DURABILITY INDEX OF SHALE INHIBITORS AND INHIBITIVE DRILLING MUD SYSTEMS

BACKGROUND OF THE INVENTION

1. Field of the Invention

Embodiments of the present invention relate in general to evaluating well drilling fluids and specifically to testing the effectiveness of the durability of inhibition of inhibitive mud systems on reactive wellbore material.

2. Description of the Related Art

In well drilling operations, drilling mud is used to lubricate the cutting surfaces and carry shale, rock, and other material ("cuttings") up through the wellbore toward the surface of the earth. As one of skill in the art will appreciate, drilling mud is commonly pumped down through the drill string, exits the drill string near the drill bit, and then returns upward through the annulus between the drill string and the wellbore or casing. In some drilling environments, the cuttings are susceptible to degradation after being cut. In particular, some types of shale can break down from a firm, rock-like material into a fine material. Such disintegration of the shale can make continued drilling more difficult. Inhibitive drilling mud can be used to prevent or delay the disintegration of the drilling mud. The inhibitive drilling mud can include chemical or polymer inhibitors that prevent the shale from disintegrating in the presence of the drilling mud. In some cases, the shale can be further degraded when it contacts non-inhibitive fluids in the wellbore. A non-inhibitive fluid is a fluid that does not inhibit the degradation of shale, and can include non-inhibitive drilling mud and reactive fluids such as water. Some inhibitive mud systems can delay the degradation of the shale in the presence of the other fluids, such as reactive fluids or non-inhibitive mud. The effectiveness of the inhibitors can vary depending on the type of shale and the type of non-inhibitive fluid.

The instantaneous and the long term inhibition of reactive shale formations while drilling is very important to avoid both immediate and time dependent borehole instability problems, especially in the presence of changing fluid environments that are reactive in nature. If the inhibition durability is insufficient, then time dependent borehole instability may occur, even though an inhibitive mud system provided excellent shale stability while drilling. This is due to the fact that the permanency of inhibition of inhibitive mud systems varies significantly due to the variation in the nature, chemistry, inhibition mechanism, inhibition longevity, etc. of the inhibitors used in the formulation of the inhibitive mud systems.

Conventional cuttings dispersion tests can provide relative ranking of the immediate effects of shale inhibition potential of various inhibitive mud systems, but they cannot predict the long term inhibition potential. Therefore, such conventional tests cannot predict the time dependent borehole stability of shale and shale cuttings subject to renewed attack of a non-inhibitive fluid. The conventional shale dispersion test described in API 13I, Section 22, for example, provides relative inhibition potential of inhibitive mud systems, but it is not an indicator of long term inhibition potential of an inhibitive mud system in changing borehole conditions. Therefore, the conventional test cannot detect, for example, that an inhibitive mud providing excellent short term inhibition while drilling may not produce a strong defense mechanism to counter the recurrent attacks of non-inhibitive fluid. The inability to detect long term effect is illustrated by the frequent failure of shale formations that have been drilled safely using an inhibitive mud when the shale comes in contact with a reactive fluid such as water or sea water.

Failures can occur in previously inhibited shale formations when subsequent contact with non-inhibitive fluid induces shale-drilling mud interactions that weaken or destroy the defensive mechanism created by the inhibitors of a previously used inhibitive mud system. Hence, the creation of a strong and durable defensive mechanism to protect the reactive shale/clays from the aging effect and also the recurrent attacks of non-inhibitive fluid are very important for instantaneous and time dependent borehole stability in reactive shale sections of a borehole. As instantaneous and short term inhibition potential of shale inhibitors and inhibitive mud systems are not the indicators of long term inhibition potential of shale inhibitors and inhibitive mud systems, the industry needs a test method and evaluation process to assess the long term inhibition potential of inhibitors and inhibitive mud systems.

It would be helpful to evaluate the permanency or longevity of inhibition, i.e. the inhibition durability limit of inhibitive muds. Unfortunately, there is no API or any other standard laboratory method to evaluate the inhibition durability index (IDI) i.e. longevity of shale inhibition to select the best shale inhibitors or inhibitive mud systems for immediate and long term stabilization of reactive shale formations.

SUMMARY OF THE INVENTION

A laboratory method and apparatus for testing and evaluating an inhibition durability limit of various inhibitors and inhibitive mud systems, which can predict the longevity of inhibition of shale inhibitors and inhibitive mud systems, is disclosed. The results of the test method can play a key role in selecting a highly effective and long lasting inhibitive mud system to preserve shale integrity to avoid time dependent borehole instability problems. The method can include an index parameter defined as an Inhibition Durability Index (IDI) to differentiate the long term inhibition potential of various inhibitive mud systems and also to develop long-life shale inhibitors for superior inhibitive drilling fluid formulation. The ability to identify muds or inhibitors with a highly durable inhibition index will not only help reduce the instantaneous borehole problems, but also help mitigate the time-dependent borehole instability. Mitigating time-dependent borehole instability is one of the key factors for safe, economic and trouble-free drilling operation from the start to the end of the well construction operation.

Embodiments of the present invention include a novel laboratory method and test set up for measuring an inhibition durability limit of different inhibitors and inhibitive mud systems to eliminate the time dependent borehole instability problems of reactive shale, mitigate the well construction cost by reducing the number of casing strings used to isolate reactive shale, and synthesize development of long-life shale inhibitors that improve the durability limit of shale inhibition. As there is no API or any other standard method that can be used to measure inhibition durability index, the embodiments of the method for predicting an inhibition durability index of shale inhibitors and inhibitive drilling mud systems can play a positive role in filling the technology gap.

Embodiments of the test method provide a test cell that mimics the conditions of a section of the borehole annulus. Inhibited shale cuttings and a non-inhibitive fluid system placed in the test cell can simulate the recurrence of shale-drilling mud interactions. Embodiments of the test method can include rotating equipment to simulate the hydro-mechanical effect along with the chemical effect while evaluating an inhibitive mud systems. Embodiments of the test method can be equally applicable for water and oil-based mud systems without any modification of the test set-up. Embodiments of the test method can define an index parameter for relative ranking of the durability limit of inhibitive mud systems and the long term inhibition potential of various inhibitors. Embodiments of the test method can provide a laboratory method for screening, evaluation and development of long life shale inhibitors to develop superior inhibitive mud system that have very high IDI values to exclude the need of extra casing strings for reactive shale isolation. Embodiments of the test method can provide a guiding tool to select the high performance and high durability inhibitors and/or inhibitive mud systems to reduce time-dependent borehole instability and well construction cost.

In embodiments of a method of evaluating a shale inhibitor, the method includes the steps of combining a predetermined quantity of drilling fluid and a predetermined quantity of earth material to define a first test mixture; placing the first test mixture in a first hot roll cell; rolling the first hot roll cell having the first test mixture in a hot roll oven at a first preselected temperature for a first predetermined amount of time; removing from the first test mixture material smaller than a preselected size to define a first remaining material; drying the first remaining material; weighing the dried first remaining material; combining at least a portion of the dried first remaining material with a non-inhibitive fluid to define a second test mixture; placing the second test mixture in a second hot roll cell; rolling the second hot roll cell having the second test mixture in the hot roll oven at a second preselected temperature for a duration t; removing from the second test mixture material smaller than a second preselected size to define a second remaining material; drying the second remaining material; weighing the dried second remaining material; and recording the weight of the dried second remaining material.

Embodiments of the method can also include the step of repeating steps and using a different duration t for each iteration. Embodiments can also include the step of plotting the weight of the dried second remaining against duration t and identifying an inflection point, the inflection point defining an inhibitive durability index. In embodiments, each step is repeated for each of a plurality of drilling fluids, and can also include the step of identifying one of the plurality of drilling fluids having the highest inhibitive durability index. In embodiments, the drilling fluid can include at least one of a chemical inhibitor and a polymer inhibitor. In embodiments, the non-inhibitive fluid can be a reactive fluid including, for example, water.

In embodiments of a method of evaluating a shale inhibitor, the method can include the steps of combining a stabilizing fluid having an inhibitor and an earth sample to define a first test mixture; subjecting the first test mixture to a simulated wellbore condition for a predetermined amount of time; drying the first test mixture; combining the dried first test mixture with a non-inhibitive fluid to define a second test mixture; subjecting the second test mixture to another simulated wellbore condition; drying the second test mixture; and determining a weight of a portion of the dried second test mixture, the portion of the dried second test mixture being greater than a preselected sieve size.

In embodiments of a method of evaluating a shale inhibitor, the method can include the steps of exposing a test material to a stability inhibitor to define an inhibited test material; performing a dispersion test to evaluate the inhibition effects of a stability inhibitor on the inhibited test material; drying the inhibited test material; exposing the dry inhibited test material to a non-inhibitive fluid; and assessing the longevity of the effect of the stability inhibitor by determining an amount of inhibited test material, greater than a preselected size, that remains after being exposed to the non-inhibitive fluid.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to embodiments thereof which are illustrated in the attached drawings, which drawings form a part of this specification. It is to be noted, however, that the drawings illustrate only a preferred embodiment of the invention and therefore should not be considered limiting of its scope as the invention may admit to other equally effective embodiments.

DETAILED DESCRIPTION OF THE INVENTION

The present invention will now be described more fully hereinafter with reference to the accompanying drawings which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, and the prime notation, if used, indicates similar elements in alternative embodiments.

Embodiments of a method for evaluating the durability of inhibition of inhibitive drilling mud systems can determine an Inhibitive Durability Index ("IDI") for each of the inhibitive mud systems. The IDI of two or more mud systems can be compared to determine which mud system is more suitable for a particular type of shale. The IDI value indicates the amount of time during which the shale cuttings maintain integrity under the detrimental action of a non-inhibitive fluid environment. Non-inhibited fluids can be a fluid that is not treated with an inhibitor or a fluid that does not have an effective concentration of an inhibitor, and can include reactive fluids such as water and saltwater. After reaching the durability time limit, the disintegration and dispersion of shale cuttings under the recurrent attack of the reactive water results in a large reduction in the mass of the inhibited cuttings.

The shield or barrier produced by an inhibitor can reduce the detrimental effect of non-inhibitive fluids, such as water molecules, on the shale cuttings for a considerable time interval. However, due to the ongoing interaction between the reactive water molecules and the shale cuttings, the barrier or shield created by the inhibitor degrades as a function of time. At the maximum inhibition durability limit, the breakdown of the defensive mechanism of the inhibitors causes serious disintegration and dispersion of the shale cuttings leading to micro-mechanical failure of the cuttings. This is illustrated in embodiments of the method by a drastic reduction in the recovered shale cuttings after the maximum inhibition durability limit. The time at which the amount of recovered shale begins to decrease is defined as the Inhibition Durability Index (IDI). The IDI indicates the maximum time to maintain the integrity of the shale cuttings under the detrimental action of the reactive fluid environment or a non-inhibitive mud environment. After the durability time limit, the disintegration and dispersion of shale cuttings under the recurrent attack of the non-inhibitive fluid causes very high loss of inhibited cuttings mass.

The equipment and tools required in embodiments of the method used to complete the testing and evaluation and determine the inhibition durability index (IDI) include typical mud laboratory equipment that are routinely used at research and rig site laboratories. The advantages of using standard equipment include eliminating the need for any new, specialized equipment, thus keeping the rig site lab compact in size. This is especially important in offshore locations because space is at a premium. By using standard equipment, no additional platform space is required. Embodiments of the test method can be performed with the following equipment:

1. Sieves. The sieves can include, for example, 8 mm, 4 mm, and 500 micron sieve sizes, a blank (pan) and a sieve shaker.
2. A controlled temperature rolling apparatus 100 (FIG. 1) that can perform room temperature and/or high temperature rolling to create the hydrodynamic effect of a borehole annulus.
3. A hot roll cell 102 (FIG. 2). The hot roll cell is a cylindrical vessel that can be used in a rolling oven. The cylindrical vessel can include, for example, a cylindrical container having an inner volume of more than 400 cc and a leak proof lid. Embodiments can also include a sealing cap and a relief device to release internal pressure after a high temperature rolling test. The cylindrical vessel can mimic conditions within a borehole annulus.
4. An oven or micro-oven for drying the cuttings after dispersion and re-dispersion tests for the designated period of time.

Embodiments of the test method used for determination of inhibition durability index ("IDI") of an inhibitive mud system can include multiple test stages, with each stage including specific steps. The first stage includes a dispersion test that evaluates the inhibition effects of a stability inhibitor after exposing the test material to the inhibitor. The second stage includes the durability inhibition assessment, which includes assessing the longevity of the effect of the inhibitor. The second stage, thus, can assess the residual effect of the inhibitor when the cuttings are exposed to a non-inhibitive fluid. A third stage can be used to graph or otherwise evaluate the results of the second stage or the first and second stages.

Figure 3:
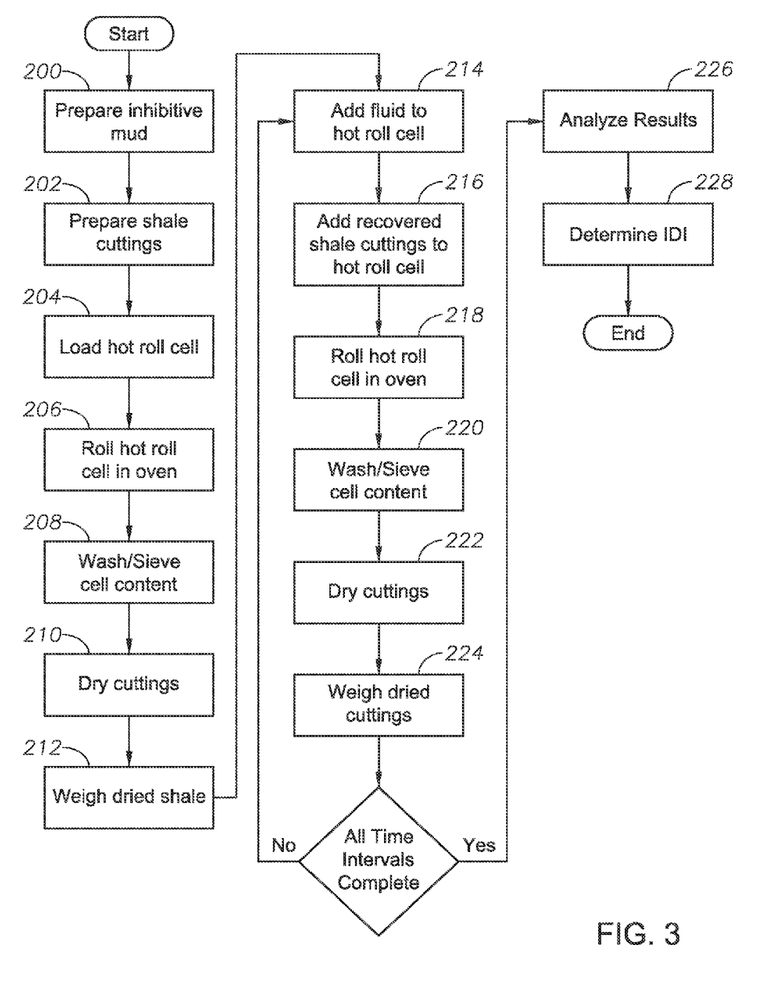
FIG. 3 is a flow-chart illustrating the steps of an exemplary embodiment of a method for predicting the inhibition durability index of shale inhibitors and inhibitive drilling mud systems.

An embodiment of a method for predicting an inhibition durability index of shale inhibitors and inhibitive drilling mud systems is illustrated in FIG. 3. In Stage 1, a dispersion test is used to assess the near term shale inhibition potential of different chemicals, polymers, and mud systems. In step 200, prepare a predetermined quantity of inhibitive mud for each mud system to be tested. Each mud system can be a predetermined quantity of drilling mud and can include an inhibitor, such as a chemical or polymer additive, thus defining an inhibitive mud. In step 202, prepare shale cuttings. The shale cuttings can be, for example, cuttings from shale cores or outcrop shale. The shale cuttings can be prepared to have a generally uniform size such as, for example, each cutting having a thickness of 4-8 mm. The initial weight of the shale cuttings can be recorded. In step 204, a predetermined quantity of shale cuttings and a predetermined quantity of inhibitive fluid, such as inhibitive mud, are placed in a hot roll cell. The shale cuttings and inhibitive fluid represent an inhibited shale formation of a borehole environment. The cap of the hot roll cell is sealingly connected to the vessel, and the hot roll cell is rolled in the oven for a predetermined duration at a predetermined temperature in step 206.

As one of ordinary skill will appreciate, parameters such as duration, temperature, and revolutions per minute ("RPM") can each be selected depending on the sample material and desired testing conditions but, preferably, the parameters are consistent for each sample being compared. Some hot roll cell ovens can heat a plurality of hot roll cells at one time and, thus, have the same parameters for each sample. In an embodiment, the hot roll cells can be rolled in an oven for 16 hours at 35 RPM. The contents of the hot roll cell are removed and sieved in step 208. The sieving process can include washing the contents with mildly running water while the contents are on a sieve, the sieve having a preselected sieve size. The shale particles smaller than the sieve size are removed, and the remaining particles that are larger than the sieve size are recovered, thus defining recovered particles. If the sieve size is 500 micron, for example, then shale pieces that are smaller than 500 micron are removed, and only shale pieces that are greater than 500 micron remain on the sieve. Those recovered particles are dried in step 210, and then weighed in step 212. The weights are recorded. The recorded weight can be used to determine the amount of shale cuttings, by weight, that were lost from the rolling and washing process by comparing the original weight to the recovered weight. The drilling mud can, however, add weight and thus must be accounted for. Steps 200-212 define Stage 1 of the method and, therefore, the weight from step 212 is referred to as the Stage 1 weight. Regardless of the initial weights, the Stage 1 weight of each of the samples can be compared to determine the relative loss from Stage 1.

The second stage of the method includes an inhibition durability assessment test for assessment of the longevity or durability of inhibition by conducting a second dispersion test (Variable Time Re-dispersion Test) for different time intervals using the already inhibited shale cuttings that were recovered after the first stage conventional dispersion test. In the second stage, a non-inhibitive fluid is used to assess the durability of inhibition of shale cuttings. The non-inhibitive fluid can be a reactive fluid such as water, a fluid that does not include an inhibitor, or a fluid that does not include an inhibitor at an effective concentration. In embodiments, water was used for aggressive interactions between inhibited shale and water or sea water that occur when simple water is used to drill a severe loss zone below a reactive shale formation. Alternatively, a non-inhibited mud can be used in the second stage.

Stage 2 includes step 214, during which a fluid, such as a reactive fluid or non-inhibitive mud, is added into a clean hot roll cell. The reactive fluid can be, for example, fresh water, salt water, or any other fluid. In embodiments, the fluid is selected to have properties similar to fluids which may contact the shale material sometime after the shale material is treated with the inhibitive mud. In step 216, a predetermined amount, by weight, of recovered shale cuttings are added to the hot roll cell. The weight can be, for example, 5 g. The recovered shale cuttings are the cuttings that were dried in step 212.

The cap of the hot roll cell is sealingly connected to the vessel, and the hot roll cell is rolled in the oven for a predetermined duration at a predetermined temperature in step 218. As one of ordinary skill will appreciate, parameters such as duration, temperature, and revolutions per minute ("RPM") can each be selected depending on the sample material and desired testing conditions but, preferably, the parameters are consistent for each sample being compared. Some hot roll cell ovens can heat a plurality of hot roll cells at one time and, thus, have the same parameters for each sample. In an embodiment, the hot roll cells can be rolled in an oven for duration t of 1-9 hours. The contents of the hot roll cell are removed and sieved in step 220. The sieving process can include washing the contents with mildly running water while the contents are on a sieve, the sieve having a preselected sieve size. The shale particles smaller than the sieve size are removed, and the remaining particles that are larger than the sieve size are recovered, thus defining recovered particles. If the sieve size is 500 micron, for example, then shale pieces that are smaller than 500 micron are removed, and only shale pieces that are greater than 500 micron remain on the sieve. Those recovered particles are dried in step 222, and then weighed in step 224. The weights are recorded. The recorded weight can be used to determine the amount of shale cuttings, by weight, that were lost from the Stage 2 rolling and washing process by comparing the original weight to the weight of the recovered shale cuttings placed into the hot roll cell in step 216. Steps 214-224 define Stage 2 of the method and, therefore, the weight from step 224 is referred to as the Stage 2 weight. Stage 2 is then repeated for different duration (t) times. For example, Stage 2 can be repeated for five iterations, with durations (t) of 1, 3, 5, 7, and 9 hours. Other durations (t) can be used. In embodiments, the Stage 2 test is repeated for multiple iterations, each using recovered shale cuttings drawn from the same batch of recovered shale cuttings from Stage 1.

In Stage 3 of the method, the data from Stages 1 and 2 are analyzed. In exemplary analyses, the variable time re-dispersion test of Stage 2 can be repeated for each of a plurality of inhibitors. In step 226, the results of the Stage 1 and Stage 2 tests, or the results of just the Stage 2 tests, are compared. For example, step 226 can include a graphical representation of the resultant data. The mass of the cuttings obtained after rolling for each of the different durations (t) can be plotted as a function of time. In step 228, the Inhibition Durability Index ("IDI") is determined. In embodiments, the IDI is the point of inflection of the mass-vs.-time curve plotted in step 226. The IDI, thus, is a measure of the amount of time during which the shale remains stable in spite of exposure to the non-inhibitive fluid.

EXPERIMENTAL DATA

A laboratory experiment was conducted to validate the method for predicting an inhibition durability index of shale inhibitors and inhibitive drilling mud systems. In the first stage of the test, 10 g of 4-8 mm size Qusaiba shale cuttings and an inhibitive drilling mud were used in the conventional dispersion test to produce more than 5 g of inhibited shale cuttings. It was assumed that inhibitive mud producing less than 5 g inhibited shale cuttings in the conventional dispersion test is not a good inhibitive mud system. Then, 5 g of inhibited shale cuttings from the cuttings recovered after the 1st stage dispersion test were used to assess the longevity of inhibition of the mud using water as a reactive fluid. The step-by-step test procedure is given below.

The 1st stage is a dispersion test. It consists of the following steps.
  a. Prepare 350 ml inhibitive mud for each of the selected mud systems using standard test equipment and procedure.
  b. Prepare 4-8 mm shale cuttings using shale cores or outcrop shales. For this development outcrop Qusaiba shale was used.
  c. Add 10 g of shale cuttings and 350 cc inhibitive drilling fluid into the hot roll cell. Screw the cap tightly and then place the cell on the roller of the hot roll oven and roll at 35 rpm for 16 hours in the first stage of inhibition permanency test.
  d. After 16 hours remove the cell from the hot roll oven and then pour the cell content into a 500 micron sieve.
  e. Wash the content of the sieve with mildly running water to remove shale pieces smaller than 500 micron.
  f. Dry the cuttings in an oven for 24 hours at 105 degrees C.
  g. Weigh the dried shale, record the dry weight and also report as a percentage of the original 10 g.

The second stage is an inhibition durability test or variable time re-dispersion test for assessment of the longevity or durability of inhibition by conducting dispersion test again for each of several different time intervals using the already inhibited shale cuttings that were recovered after the first stage conventional dispersion test. In this stage water is used as a representative of the most aggressive fluid to assess the durability of inhibition of shale cuttings.
  a. Pour 350 cc fresh water into the hot roll cell again to represent a highly reactive fluid environment.
  b. Place 5 g dried shale cuttings that were recovered after first stage dispersion test into the fresh water of the hot roll cell
  c. Place the cell in the rolling oven and roll for 1 to 9 hours using several inhibited cuttings samples inhibited by the same inhibitive mud system.
  d. After rolling for the designated time period, pour the contents into a 500 micron sieve and wash using mild running water to remove particles below 500 microns.
  e. Measure the weight after drying at 105 degrees C for 24 hours and record the weight.
  f. Repeat Stage 2 using different time periods in step d.
  g. Plot the mass recovered from each iteration as a function of rolling time.

The third stage of the test is the graphical representation of the second stage test results as a function of time to determine the Inhibition Durability Index (IDI) as the point of inflection of the curve.

The following data shows a comparison of effectiveness of each two inhibitive mud systems over time, in the presence of a non-inhibitive fluid. According to the experimental data shown in FIG. 4, the inhibitive Mud 1 inhibited the reactive shale cuttings effectively and thus created a strong and high resistance barrier or protective shield around the shale cuttings. The shield or barrier produced by the inhibitors reduced the detrimental effect of reactive water molecules to the shale cuttings for a considerable time interval. However, due to the ongoing interaction between the reactive water molecules and the shale cuttings, the barrier or shield created by the inhibitors degrades with increasing time of interactions. At the maximum inhibition durability limit, the breakdown of the defensive mechanism of the inhibitors causes serious disintegration and dispersion of the shale cuttings leading to micro-mechanical failure of the cuttings. This is reflected by a drastic reduction in the recovered shale cuttings after the maximum inhibition durability limit. The inflection point in the remaining cuttings mass versus rolling time curve shown in FIG. 4 indicate the maximum inhibition time limit of inhibitive Mud 1. The time representing this limiting point is defined as the Inhibition Durability Index (IDI). The IDI indicates the maximum time to maintain shale cuttings integrity under the detrimental action of the non-inhibitive fluid environment. After the durability time limit, the disintegration and dispersion of shale cuttings under the recurrent attack of the reactive water causes very high loss of inhibited cuttings mass.

Figure 4:
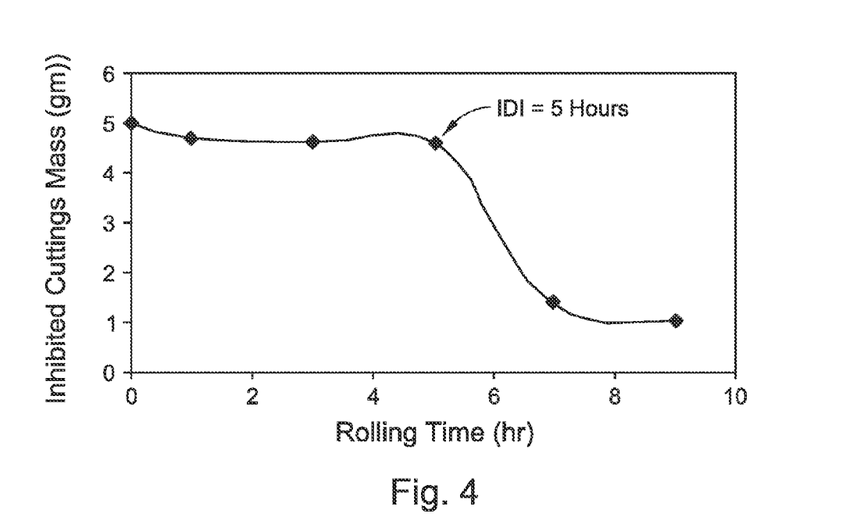
FIG. 4 is a graph showing the recovered mass versus the rolling time curve of inhibited shale cuttings that were inhibited by an inhibitive mud in an experimental application of an exemplary embodiment of a method for predicting the inhibition durability index of shale inhibitors and inhibitive drilling mud systems.
Figure 5:
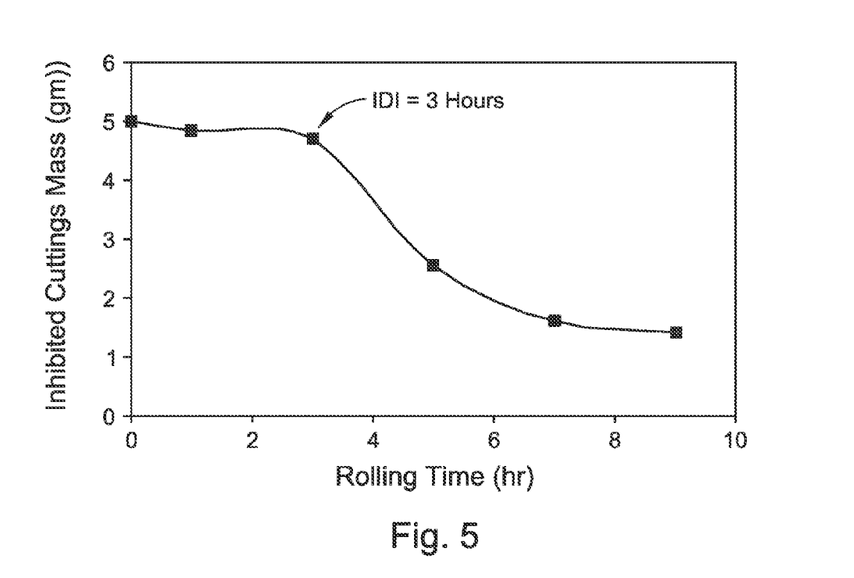
FIG. 5 is a graph showing the recovered mass versus the rolling time curve of inhibited shale cuttings that were inhibited by another inhibitive mud in an experimental application of an exemplary embodiment of a method for predicting the inhibition durability index of shale inhibitors and inhibitive drilling mud systems.

Experimental data presented in FIG. 5 shows the test results of shale cuttings inhibited by inhibitive Mud 2. Due to the weaker and relatively short lived inhibition of the cuttings by inhibitive Mud 2, the shale cuttings disintegrated and dispersed significantly after three hours of recurrent attack by reactive water. Therefore, Mud 2 produced a lower Inhibition Durability Index (IDI) compared to Mud 1 (see FIGS. 4 and 5). The data clearly demonstrates the relative longevity of inhibition of the two inhibited mud systems by showing an IDI value of 5 hours for Mud 1 and an IDI value of 3 hours for Mud 2 and thus validate the test method disclosed in the current invention. The following explanation describes the method of determining the IDI for Mud 1 and Mud 2.

To evaluate Mud 1, 10 g of Qusaiba shale cuttings were rolled for 16 hours in a hot roll oven at room temperature in the presence of inhibitive Mud 1. Due to inhibition of the shale cuttings by the inhibitors used in the mud formulation, only minor amounts of cuttings were lost when washed using a 500 micron sieve to remove disintegrated particles smaller than 500 microns (see Table 1).

TABLE 1

Experimental Data Showing Shale Dispersion Test Results.

| Mud System | Dry Shale Cuttings Weight (g) | | |
|---|---|---|---|
| | Initial Weight 1 | Final Weight after Dispersion Test | Remark |
| Inhibitive Mud 1 | 10 | 9.49 | 5 g of inhibited Cuttings were used for Inhibition Durability Assessment |
| Inhibitive Mud 2 | 10 | 9.19 | |

The amount of cuttings recovered after the dispersion test is more than 9 g. Then, 5 g of the recovered 9 g of shale cuttings were poured into the hot roll cell and rolled for 1, 3, 5, 7 and 9 hours in the presence of 350 cc water to evaluate the durability of inhibition of the inhibitive Mud 1. After the tests, the mass recovered for each of the designated rolling times was recorded and plotted as a function of time. Table 2 shows the rolling time versus the remaining cuttings mass (dry) after Stage 2 exposure to fresh water to simulate a reactive fluid environment.

TABLE 2

Experimental data showing Rolling Time versus Remaining Cuttings Mass (Dry) in the Presence of Fresh Water Used to Simulate a Reactive Fluid Environment

| | Dry Weight (g) | |
|---|---|---|
| Rolling Time (hour) | Shale Cuttings Inhibitive by Inhibitive Mud 1 | Shale Cuttings Inhibitive by Inhibitive Mud 2 |
| 0 | 5 | 5 |
| 1 | 4.68 | 4.84 |
| 3 | 4.58 | 4.68 |
| 5 | 4.52 | 2.54 |
| 7 | 1.27 | 1.61 |
| 9 | 1.02 | 1.41 |

FIG. 4 shows the recovered mass versus the rolling time curve of inhibited shale cuttings that were inhibited by inhibitive Mud 1. FIG. 4 thus shows the IDI value of inhibitive Mud 1. The data clearly shows that there is a drastic reduction in recovered cuttings mass after 5 hours of interactions with water used to create the hydrodynamic effect and chemical interaction of shale cuttings in the annulus. The curve of the line connecting the data points is relatively stable through the 5 hour point, and then begins sloping downward. The 5 hour point, thus, is an inflection point that defines the IDI value. The plot, thus, shows the IDI value of the inhibitive mud system is about 5 hours. Hence, the Mud 1 has an inhibition durability index equal to 5 hours.

To evaluate Mud 2, as before, 10 g Qusaiba shale cuttings were rolled for 16 hours in a hot roll oven at room temperature in the presence of inhibitive Mud 2. Due to inhibition of the shale cuttings by the inhibitors used in the mud formulation, only minor amounts of cuttings were lost when washed using a 500 micron sieve to remove disintegrated particles smaller than 500 microns (see Table 1). The amount of cuttings recovered after the dispersion test is more than 9 g. Then, 5 g of the recovered 9 g of shale cuttings were poured into the hot roll cell and rolled for 1, 3, 5, 7 and 9 hours in the presence of 350 cc water to evaluate the durability of inhibition of the inhibitive Mud 2. After the tests, the mass recovered for each of the designated rolling times was plotted as a function of time. FIG. 5 shows the recovered mass versus the rolling time curve of inhibited shale cuttings that were inhibited by inhibitive Mud 2. FIG. 5 thus shows the IDI value of inhibitive mud. The data clearly shows that there is a drastic reduction in recovered cuttings mass after 3 hours of interactions with water used to create the hydrodynamic effect and chemical interaction of shale cuttings in the annulus. This plot shows an inflection point at the 3 hour duration and, thus, the IDI value of the inhibitive mud system is about 3 hours. Hence, the Mud 2 has an inhibition durability index equal to 3 hours.

Figure 1:
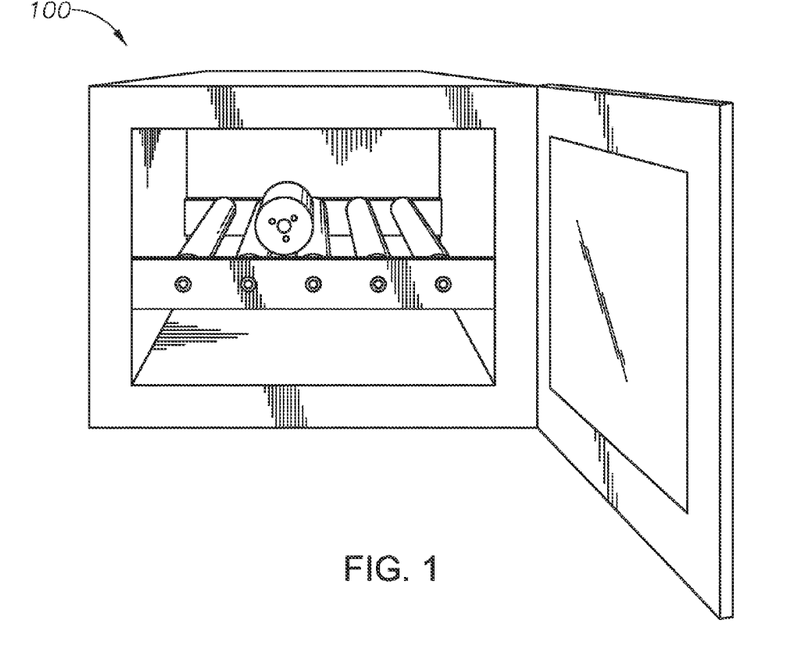
FIG. 1 is a front environmental view of an embodiment of a controlled temperature rolling apparatus for rolling a hot roll cell at a preselected temperature.
Figure 2:
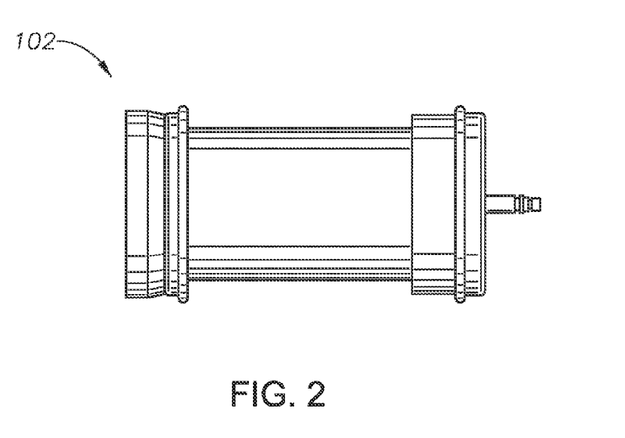
FIG. 2 is a side environmental view of the hot roll cell of FIG. 1.

The validation test results show that Mud 1 produced higher Inhibition Durability Index (IDI) compared to Mud 2 (see FIGS. 1 and 2). The remaining mass versus rolling time plot of Mud 1 shows an IDI value of 5 hours. After 5 hours of effective defense against the non-inhibitive fluid, the inhibitors failed to preserve the cuttings integrity. Hence, the shale cuttings disintegrated and dispersed easily leading to a drastic reduction in remaining cuttings mass. Mud 2 has the IDI value of 3 hours which is 2 hours less than Mud 1.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within the said range.

Throughout this application, where patents or publications are referenced, the disclosures of these references in their entireties are intended to be incorporated by reference into this application, in order to more fully describe the state of the art to which the invention pertains, except when these reference contradict the statements made herein.

What is claimed is:

1. A method of evaluating a shale inhibitor, the method comprising the steps of:
   (a) combining a predetermined quantity of drilling fluid and a predetermined quantity of earth material to define a first test mixture;
   (b) placing the first test mixture in a first hot roll cell;
   (c) rolling the first hot roll cell having the first test mixture in a hot roll oven at a first preselected temperature for a first predetermined amount of time;
   (d) removing from the first test mixture material smaller than a preselected size, the remaining material defining a first remaining material;
   (e) drying the first remaining material;
   (f) weighing the dried first remaining material;
   (g) combining at least a portion of the dried first remaining material with a non-inhibitive fluid to define a second test mixture;
   (h) placing the second test mixture in a second hot roll cell;
   (i) rolling the second hot roll cell having the second test mixture the hot roll oven at a second preselected temperature for a duration time (t);
   (j) removing from the second test mixture material smaller than a second preselected size, the remaining material defining a second remaining material;
   (k) drying the second remaining material;
   (l) weighing the dried second remaining material;
   (m) recording the weight of the dried second remaining material;
   repeating steps (g) through (m), wherein the duration (t) is a different amount of time for each iteration; and
   plotting the weight of the dried second remaining material against the duration (t) for each iteration, and identifying an inflection point, wherein the inflection point defines an inhibitive durability index.

2. The method according to claim 1, wherein each step is repeated for each of a plurality of drilling fluids, and further comprising the step of identifying one of the plurality of drilling fluids having, the highest inhibitive durability index.

3. The method according to claim 1, wherein the drilling fluid comprises at least one of a chemical inhibitor and a polymer inhibitor.

4. The method according to claim 1, wherein the non-inhibitive fluid comprises water.

5. A method of evaluating a shale inhibitor, the method comprising the steps of:
   (a) combining a stabilizing fluid having an inhibitor and an earth sample to define a first test mixture;
   (b) subjecting the first test mixture to a simulated wellbore condition for a predetermined amount of time;
   (c) drying the first test mixture;
   (d) combining the dried first test mixture with a non-inhibitive fluid to define a second test mixture;
   (e) subjecting the second test mixture to another simulated wellbore condition;
   (f) drying the second test mixture;
   (g) determining a weight of a portion of the dried second test mixture, the portion of the dried second test mixture being greater than a preselected sieve size;
   repeating steps (d) through (g), wherein the duration (t) is different for each iteration; and
   plotting the weight of the dried second test mixture against the duration (t) for each iteration, and identifying an inflection point, wherein the inflection point defines an inhibitive durability index.

6. The method according to claim 5, wherein each step is repeated for each of a plurality of stabilizing fluids, and further comprising the step of identifying one of the plurality of stabilizing fluids having a highest inhibitive durability index.

7. The method according to claim 5, wherein the stabilizing fluid is a drilling fluid.

8. The method according to claim 5, wherein the stabilizing fluid comprises an inhibitor.

9. The method according to claim 5, wherein the simulated wellbore condition comprises rolling the test mixture in a hot roll cell.

10. A method of evaluating a shale inhibitor, the method comprising the steps of:
    (a) exposing a test material to a stability inhibitor to define an inhibited test material;
    (b) performing a dispersion test to evaluate the inhibition effects of a stability inhibitor on the inhibited test material;
    (c) drying the inhibited test material;
    (d) exposing the dry inhibited test material of step (c) to a non-inhibitive fluid;
    (e) assessing the longevity of the effect of the stability inhibitor by determining an amount of inhibited test material, greater than a preselected size, that remains after being exposed to the non-inhibitive fluid;
    repeating steps (d) and (e) for a plurality of iterations, wherein the duration of step (d) is different for each iteration; and
    plotting the amount of the inhibited test material remaining after being exposed to the non-inhibitive fluid against the duration of step (d) for each of the plurality of iterations.

11. The method according to claim 10, further comprising the step of determining an inflection point, the inflection point being the beginning of a downward slope of a line connecting each of the plotted amounts of remaining inhibited test material, the inflection point defining an inhibition durability index.

12. The method according to claim 11, wherein each step is repeated for each of a plurality of stability inhibitors.

13. The method according to claim 12, further comprising the step of identifying one of the plurality of stability inhibitors having the longest stability duration, the longest stability duration being defined by the largest inhibition durability index.

14. The method according to claim 10, wherein step (d) comprises rolling the test material and non-inhibitive fluid in a hot cell rolling oven, at a preselected temperature.

* * * * *

UNITED STATES PATENT AND TRADEMARK OFFICE
CERTIFICATE OF CORRECTION

| | | |
|---|---|---|
| PATENT NO. | : 9,164,018 B2 | Page 1 of 1 |
| APPLICATION NO. | : 13/854638 | |
| DATED | : October 20, 2015 | |
| INVENTOR(S) | : Md Amanullah, Mohammed Al-Arfaj and Adel Al-Ansari | |

It is certified that error appears in the above-identified patent and that said Letters Patent is hereby corrected as shown below:

In the Claims

In Column 11, Line 57, Claim 2, the third word appears as "having," and should read --having--.

In Column 12, Line 65, Claim 14, the fifth word appears as "oven," and should read --oven--.

Signed and Sealed this
Twenty-second Day of March, 2016

Michelle K. Lee
*Director of the United States Patent and Trademark Office*